United States Patent [19]

Amkraut

[11] Patent Number: 5,049,387
[45] Date of Patent: Sep. 17, 1991

[54] INDUCING SKIN TOLERANCE TO A SENSITIZING DRUG

[75] Inventor: Alfred Amkraut, Palo Alto, Calif.

[73] Assignee: Alza Corporation, Palo Alto, Calif.

[21] Appl. No.: 364,932

[22] Filed: Jun. 9, 1989

Related U.S. Application Data

[63] Continuation-in-part of Ser. No. 217,014, Jul. 8, 1988, Pat. No. 5,000,956.

[51] Int. Cl.$^5$ .............................................. A61F 13/00
[52] U.S. Cl. .................................... 424/435; 424/448; 424/449
[58] Field of Search ...................... 424/449, 448, 435; 421/447, 449, 448

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 4,130,643 | 12/1978 | Smith | 424/238 |
| 4,144,317 | 3/1979 | Higuchi et al. | 424/21 |
| 4,286,592 | 9/1981 | Chandrasekaran | 128/260 |
| 4,292,303 | 9/1981 | Keith et al. | 424/28 |
| 4,314,557 | 2/1982 | Chandrasekaran | 128/260 |
| 4,343,798 | 8/1982 | Fawzi | 424/240 |
| 4,353,896 | 10/1982 | Levy | 424/195 |
| 4,362,737 | 12/1982 | Schafer et al. | 424/273 |
| 4,379,454 | 4/1983 | Campbell et al. | 604/897 |
| 4,548,922 | 10/1985 | Carey et al. | 514/4 |
| 4,559,222 | 12/1985 | Enscore et al. | 424/28 |
| 4,573,995 | 3/1986 | Cheng et al. | 604/896 |
| 4,608,249 | 8/1986 | Otsuka et al. | 424/28 |
| 4,634,766 | 1/1987 | Atkinson et al. | 544/34 |
| 4,666,441 | 5/1987 | Audriolo et al. | 424/448 |
| 4,885,154 | 12/1989 | Cormier et al. | 514/647 |

FOREIGN PATENT DOCUMENTS

| | | |
|---|---|---|
| 0159168A2 | 10/1985 | European Pat. Off. |
| 0196762 | 10/1986 | European Pat. Off. |
| 0040861A1 | 12/1986 | European Pat. Off. |
| 60-23312 | 2/1985 | Japan . |
| WO8809175 | 12/1988 | PCT Int'l Appl. |

OTHER PUBLICATIONS

Drug Information 86, 84:06 "Anti-Inflammatory Agents: Topical Corticosteroids General Statement" pp. 1780–1782, American Hospital Formulary Service.

J. Foussereau, C. Benezra, H. I. Maiback & N. Hjortn, "Occupational Contact Dermatitis, Clinical and Chemical Aspects," (W. B. Saunders Company 1982).

B. W. Barry and D. I. D. El Eini, "Influence of non-ionic surfactants on permeation of hydrocortisone, dexamethasone, testosterone and progesterone across celluacetate membrane," J. Pharm. Pharmac. 28, pp. 219–227 (1976).

D. V. Belsito et al, "Effect of Glucocorticosteroids on Epidermal Langerhans Cells," J. Exp. Med., vol. 155, pp. 291–302 (Jan. 1982).

M. M. Burrows et al, "Inhibition of Induction of Human Contact Sensitization by Topical Glucocorticosteroid," Arch Dermatol, vol. 112, pp. 175–178 (Feb. 1986).

B. Berman et al, "Modulation of Expression of Epidermal Langerhans Cell Properties Following in Site Exposure to Glucocorticosteroids," The Journal of Investigative Dermatology, vol. 80, No. 3, pp. 168–171 (1983).

(List continued on next page.)

*Primary Examiner*—Thurman K. Page
*Assistant Examiner*—Leon R. Horne
*Attorney, Agent, or Firm*—D. Byron Miller; Edward L. Mandell; Steven F. Stone

[57] ABSTRACT

A method of inducing immune tolerance to a drug which is normally sensitizing to humans when applied to human skin or mucosa is provided. The sensitizing drug is continuously and co-extensively administered to a selected skin or mucosa site with the corticosteroid. Preferably, the corticosteroid is hydrocortisone or an ester thereof. The corticosteroid is administered to the selected skin or mucosa site at a rate and for a period of time sufficient to induce tolerance to the drug. Thereafter, the drug can be administered to the human, without administering any corticosteroid, without danger of inducing sensitization to the drug in the human.

36 Claims, 1 Drawing Sheet

OTHER PUBLICATIONS

J, Fachet et al, "Effect of Corticosteroids and Adult Thymectony on Induction and Recall of Contact sensitivity in Mice," Clin. Exp. Immunol 10, pp. 661-692 (1972).

Geoffrey Zubay, Biochemistry, pp. 535-543 (1983).

B. Samuelsson, "Leubotrienes: Mediators of Immediate Hypersensitivity Reactions and Inflammation," Science, vol. 220, pp. 568-575 (May 1983).

AMA drug Evaluations, 5th edition, pp. 1441-1442.

Dermatitis and Nitroglycerin—Hendricks & Dec. vol. 115, Jul., 1979, pp. 853-855.

"Local Effects of Ultraviolet Radiation on Immune Function in Mice," Bergstresser, Elimets, Streilein, Department of Dermatology, Internal Medicine and Cell Biology, U. of Texas Health and Science Center at Dallas, pp. 73-86.

Physicians' Desk Reference—copyright 1987.

"Relationship Between Epidermal Langerham Cell Density ATPase Activity and the Induction of Contact Hypersensitivity," vol. 126, No. 5, May/81 The Journal of Immunology, pp. 1892-1897.

"Local Effects of UV Radiation on Immunization with Contact Sensitizers" Photodermotalogy, 1988 5: 126-132.

"Modulation of the Population Density of Identified Epidermal Langerhans Cells Associated with Enhancement or Suppression of Cutaneous Immune Reactivity," The Journal of Immunology, vol. 136, No. 3, pp. 867-876.

"Anti—Inflammatory Properties of an Oxidized Sterol" the Journal of Investigative Dermatology, vol. 1 84, No. 2.

"Over—Dose Management of Contact Sensitivity to Chlorpromazine," R. M. Morris—Owen Registran, Allergy Clinic, Radcliffe Infirmary, Oxford, pp. 167-169.

"Monographs in Allergy, vol. 15, Immunological Aspects of Control Sensitivity," L. Polak, pp. 64-169.

"Reactions from Systemic Exposure to Contact Allergens," Seminarsin Dermatology vol. 1, No. 1, Mar. 1982, pp. 15-23.

"The Effect of Selected Immunomodulating Agents on Experimental Contact Reactions," Christopher Anderson, Department of Dermatology, Linkoping University, Linkoping, Sweden, pp. 4-47.

"New Keys to Cosmotic Chemisty," pp. 49-65, Paul G. Lauffer, Cosmetics & Toiletries.

"Evaluation and Relevance of Skin Sensitivity in Animal Models," British Journal of Dermatology (1986) 115, supplement 31, pp. 24-32.

Facts and Comparisons®, pp. 597-600, 1986, J. B. Lippincott, Co.

INDUCING SKIN TOLERANCE TO A SENSITIZING DRUG

CROSS-REFERENCE TO RELATED APPLICATIONS

The present invention is related to U.S. patent application Ser. No. 023,583 filed Mar. 9, 1987, now abandoned and U.S. patent application Ser. No. 217,014 filed July 8, 1988.

BACKGROUND OF THE INVENTION

1. Field of the Invention

This invention relates to the transdermal delivery of drugs. More particularly, this invention relates to preventing contact sensitization to a skin sensitizing drug by inducing tolerance to the drug.

2. Description of the Prior Art

The transdermal route of parenteral drug delivery provides many advantages and transdermal systems for delivering a wide variety of drugs and other beneficial agents are known and described in U.S. Pat. Nos. 3,598,122; 3,598,123; 4,286,592; 4,314,557; 4,379,454; 4,559,222 and 4,573,995, for example, all of which are incorporated herein by reference.

Unfortunately however, many drugs which appear to be ideal candidates for transdermal delivery have a tendency to sensitize human patients. This is especially true for drugs which are transdermally or transmucosally administered for sustained periods of time. The sensitizing drugs can cause undesirable skin reactions, a condition known as contact sensitivity or contact allergy. Therefore, despite the development of the transdermal drug delivery art, there remains a continuing need for an improved method of overcoming contact sensitization caused by transdermal or transmucosal delivery of a sensitizing drug.

Sensitization is a two-phase process involving distinct biological mechanisms of the human immune system. The first phase is called the induction phase. Induction occurs when the skin of individual is first exposed to the sensitizing drug. In this phase, the sensitizing drug or antigen is presented to the T-lymphocytes (T-cells) by the Langerhans cells of the epidermis, either in situ or in the draining lymph node. As a consequence, T-cells which recognize the antigen, proliferate and to some extent differentiate. Generally, no visible skin reaction is noted during the induction phase. Following induction, the individual's lymphocytes are specifically sensitized to the drug.

The second phase of sensitization is called elicitation. Elicitation occurs when the individual is subsequently (i.e., after induction) exposed to the same sensitizing drug. Elicitation causes a skin reaction to occur. The skin reaction occurring during elicitation is known as contact dermatitis. During elicitation, the antigen is once again presented mainly on the Langerhans cells. The T-cells, which have proliferated upon prior exposure to the drug (i.e., during the induction phase), now come to the treated site and initiate toxic events which result in local inflammation (i.e., contact dermatitis).

Irritation on the other hand is a completely different phenomenon from contact (i.e., skin) sensitization. Skin irritation can be caused by a variety of factors including, but not limited to, physical factors (e.g., chafing or occluding the skin in an air-tight manner), exposure to certain chemicals, exposure to pH outside the normal pH range of the skin or mucosa and bacterial overgrowth. Generally, irritation is the result of damage to cells in the skin or mucosa caused by their response to a toxic (i.e., irritating) agent. Sensitization on the other hand, is the result of a response by the immune system to an agent (i.e., an antigen) which is not necessarily irritating.

Corticosteroids are known anti-inflammatory agents and are commonly used to alleviate the skin reactions occurring during the elicitation phase of sensitization and to alleviate the after-effects of skin irritation. For example, corticosteroids have been administered with another drug, such as an antibiotic, in order to treat existing inflammation at the site of a skin infection. See Fawzi U.S. Pat. No. 4,343,798.

Investigators have found that corticosteroids are effective in reducing and/or preventing skin irritation in guinea pigs and rabbits caused by skin occlusion. For example, in Japanese Kokai No. 60-23,312, Nitto Electric Ind. Co. (1985), corticosteroids are delivered from a transdermal skin patch. Nitto teaches that when the patch is applied to the skin in an air-tight manner, the barrier properties of the skin are reduced thereby making it easier for the drug to permeate through the skin. Nitto further teaches that (i) these air-tight skin patches do not allow moisture from the skin to evaporate, and (ii) the retained moisture eventually causes inflammation. Nitto delivers a small amount of an anti-inflammatory corticosteroid, together with the drug, in order to reduce the inflammation caused by the moisture retained in the skin.

Immune tolerance is a different phenomenon from both sensitization and irritation. Immune tolerance is the state of prolonged unresponsiveness to a specific antigen. Tolerance has been induced experimentally in several animal species by administration of the antigen to fetal or neonatal animals. Tolerance can also be induced for certain antigens by injecting the antigen in a non-immunizing form. This has been accomplished for example with gamma globulin cleared of aggregates by extensive high speed centrification. In addition, tolerance to contact sensitization has been induced in adult animals (i) by pretreatment of the skin site to which the sensitizing antigen is applied with compounds which act to suppress the animal s immune system (See The Journal of Immunology, Vol. 136, No. 3, Rheins & Nordlund, pp. 867-876, (1986)) or (ii) by UV irradiation (See Photodermatology, Vol. 5, Cruz et al, pp. 126-132 (1988)). Immune tolerance to contact sensitizers was induced in mice by delivering several doses of UV irradiation (Cruz et al) or by application of arachidonic acid to the local site for several days prior to antigen application (see Rheins & Nordlund). In the later study, a systemic effect on the entire immune system of the mice, rather than any local effect, was not ruled out. However, other investigators have found that while immune tolerance could be induced in certain strains of mice by UV irradiation, in other strains of mice tolerance could not be so induced. See The Effect of Ultraviolet Radiation on the Immune System, chapter 5, Bergstresser et al, pp. 73-86 (1983). Clearly then it is difficult to predict whether or not immune tolerance can be induced topically in different animal strains. Those skilled in the art of skin sensitization can readily appreciate the difficulty in predicting the occurrence of immune tolerance by extrapolating from one animal species to another. Other investigators have found that pretreating human skin with betamethasone valerate can prevent induction of sensitization to a normally sensitizing compound (e.g., dinitrochlorobenzene). See Arch. Dermatol., vol. 112, Burrows et al, pp. 175-8 (1976). However, these same investigators failed to induce tolerance to dinitrochlorobenzene.

In general, once the skin has become sensitized, skin reactions occurring after re-exposure to the sensitizing agent are difficult if not impossible to prevent. For that reason, this invention is directed towards preventing sensitization from occurring, rather than treating problems of pain and discomfort occurring during the elicitation phase (i.e, after sensitization has already been induced).

SUMMARY OF THE INVENTION

Therefore, it is an object of the present invention to prevent sensitization in a human patient caused by the transdermal/transmucosal administration to the patient of a sensitizing drug.

It is a further object of the present invention to prevent sensitization in a human patient by inducing tolerance to a sensitizing drug during the transdermal/transmucosal administration of the drug to the patient.

These and other objects are met by the present invention which provides a method of preventing skin sensitization by inducing immune tolerance to a drug in a human. The drug is sensitizing to humans, i.e., the drug is susceptible to inducing skin or mucosa sensitization in a human when the drug is transdermally or transmucosally administered to the human at a therapeutically effective rate. Immune tolerance is induced by the steps of:

(a) continuously and co-extensively administering to the skin or mucosa of the human:
(1) the drug, to a selected skin or mucosa site, at a therapeutically effective rate and over a predetermined delivery period; and
(2) a corticosteroid, the corticosteroid being administered to the selected site (i) at a rate and (ii) for a period of time sufficient to induce immune tolerance to the drug in the human; and thereafter
(b) discontinuing the transdermal or transmucosal administration of the corticosteroid to the human; and
(c) transdermally or transmucosally readministering the drug, without administering any corticosteroid, to the human, the drug being readministered at a therapeutically effective rate and over a period of time sufficient to maintain the induced immune tolerance in the human.

In one embodiment of the present invention, tolerance to a weakly sensitizing drug may be achieved by administering a single transdermal or transmucosal drug delivery system to a selected site on the skin or mucosa of a human. A single transdermal or transmucosal drug delivery system is suitable for inducing tolerance to a drug in accordance with the present invention only when the drug is weakly sensitizing and immune tolerance to the drug can be induced before the expiration of the delivery life of the system. The system comprises a matrix adapted to be placed in drug and corticosteroid transmitting relation to the selected skin or mucosa site. The matrix contains sufficient amounts of drug and corticosteroid to continuously and co-extensively administer to the skin or mucosa site:

(1) the drug, at a therapeutically effective rate and over a predetermined delivery period; and (2) the corticosteroid, the corticosteroid being administered (i) at a rate and (ii) for a period of time sufficient to induce immune tolerance in the human. The amounts of drug and corticosteroid provided in the matrix are such that the drug is delivered for a longer period than the corticosteroid, i.e., the predetermined delivery period is longer than the period of time sufficient to induce immune tolerance to the drug. Accordingly, after immune tolerance is induced but before the matrix stops administering drug, the matrix stops administering the corticosteroid and thereafter the matrix administers only the drug to the human at a therapeutically effective rate and for a period of time sufficient to maintain the induced immune tolerance in the human.

DETAILED DESCRIPTION OF THE INVENTION

According to the present invention, selected regimens of continuous and co-extensive transdermal or transmucosal administration of a corticosteroid with a normally sensitizing drug prevents sensitization in humans by inducing tolerance to the drug. In order to achieve the advantages of the present invention, the corticosteroid is co-extensively administered with the drug at the same skin or mucosa site where the drug is being administered (1) at a rate and (2) for a period of time sufficient to induce immune tolerance to the drug in the human. Once immune tolerance to the drug has been induced through co-extensive administration of the drug with the corticosteroid, the administration of corticosteroid may be stopped and thereafter the sensitizing drug administered without any corticosteroid and without danger of sensitizing the patient and causing adverse skin reactions.

Once immune tolerance has been induced by co-extensively administering the drug and corticosteroid, the sensitizing drug may be thereafter administered following an administration regimen which is sufficient to maintain the induced tolerance in the individual patient. Generally, continuous readministration of the sensitizing drug after the induction of sensitization will maintain the induced tolerance in the individual patient. However, in many instances continuous readministration of the drug is not necessary to maintain induced tolerance to the drug. Depending upon a number of factors including the particular drug being administered and the individual patient, intermittent readministration of the sensitizing drug after tolerization may be sufficient to maintain tolerance. Thus, once tolerance has been induced, the re-application of the sensitizing drug without corticosteroid for periods on the order of several weeks out of a period extending over about 6 to 12 months is in many cases sufficient to maintain the induced tolerance in the individual patient.

In order to ensure co-extensive administration of drug and corticosteroid, it is preferred to administer the drug and corticosteroid from a solid matrix (e.g., a drug and corticosteroidcontaining matrix) in a transdermal or transmucosal delivery system, which matrix is placed in drug and corticosteroid transmitting relationship to the skin or mucosa.

Figure 1:
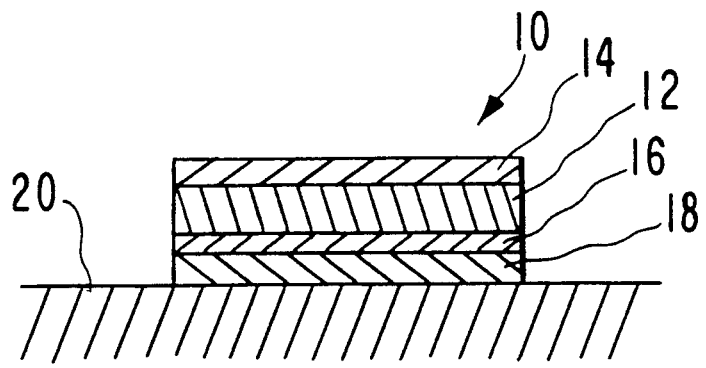
FIG. 1 is a cross-sectional view of one embodiment of a transdermal therapeutic system which may be used in accordance with the present invention.
Figure 2:
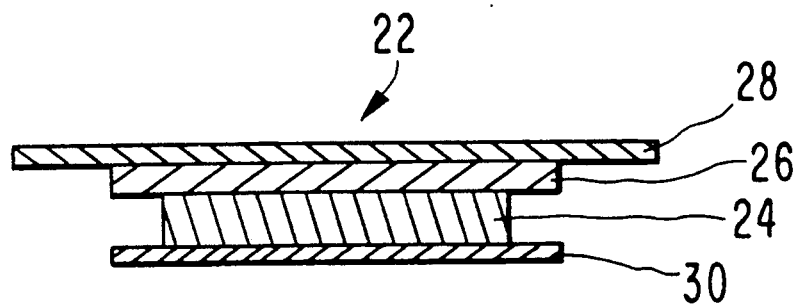
FIG. 2 is a cross-sectional view of another embodiment of a transdermal therapeutic system which may be used in accordance with the present invention.

Two examples of suitable transdermal delivery systems are illustrated in FIGS. 1 and 2. Referring specifically to FIG. 1, transdermal delivery system 10 comprises a reservoir 12 containing both a sensitizing drug and a corticosteroid. Reservoir 12 is preferably in the form of a matrix containing the drug and corticosteroid dispersed therein. Reservoir 12 is sandwiched between a backing layer 14, which is impermeable to both the drug and the corticosteroid, and a rate controlling membrane 16. The system 10 adheres to the surface of the skin 20 by means of an in-line contact adhesive layer 18. The adhesive layer 18 may optionally contain corticosteroid and/or drug. A strippable release liner (not shown), is normally provided along the exposed surface of adhesive layer 18 and is removed prior to application of system 10 to the skin 20.

Alternatively as shown in FIG. 2, the transdermal therapeutic system 22 may be attached to the skin of a patient by means of an adhesive overlay 28. System 22 is comprised of a sensitizing drug and corticosteroid-containing reservoir 24 which is preferably in the form of a matrix containing the drug and the corticosteroid dispersed therein. An impermeable backing layer 26 is provided adjacent one surface of reservoir 24. Adhesive overlay 28 maintains the system on the skin and may be fabricated together with, or provided separately from, the remaining elements of the system. With certain formulations, the adhesive overlay 28 may be preferable to the in-line contact adhesive 18 as shown in FIG. 1. This is true for example, where the drug/steroid reservoir contains a material (e.g., an oily surfactant permeation enhancer) which adversely affects the adhesive properties of the in-line contact adhesive layer 18. Impermeable backing layer 26 is preferably slightly larger than reservoir 24, and in this manner prevents the materials in reservoir 24 from adversely interacting with the adhesive in overlay 28. Optionally, a rate controlling membrane (not shown in FIG. 2) similar to membrane 16 may be provided on the skin side of reservoir 24. A strippable release liner 30 is also provided with system 22, and removed just prior to application of system 22 to the skin.

The method of the present invention requires no pretreatment of the skin site with corticosteroid. The corticosteroid can be delivered from the drug reservoir and/or other drug releasing component of the transdermal drug delivery system. For example with certain drug/corticosteroid combinations, the drug flux is much greater than the corticosteroid flux. In such cases, the corticosteroid is preferably present in the adhesive layer 18. On the other hand, where there is no great disparity between drug and corticosteroid fluxes, both the drug and the corticosteroid may be delivered from the reservoirs 18 and 24.

The drug and the corticosteroid can be co-extensively administered to human skin or mucosa from a skin patch or other known transdermal/transmucosal delivery system which contains a saturated or unsaturated formulation of the drug and the corticosteroid. The formulation may be aqueous or non-aqueous based. The formulation should be designed to deliver the sensitizing drug and the corticosteroid at the necessary fluxes. Depending on the drug to be delivered, the drug and corticosteroid carrier(s) may be either aqueous or non-aqueous (e.g., oil) based. Aqueous formulations, specifically gels, typically comprise water and about 1-2 weight % of hydrophilic polymer as a gelling agent, such as hydroxyethyl cellulose or hydroxypropyl cellulose. Typical non-aqueous gels are comprised of silicone fluid or mineral oil. Mineral oil-based gels also typically contain 1-2 weight % of a gelling agent such as colloidal silicon dioxide. The suitability of a particular gel depends upon the compatibility of its constituents with both the sensitizing drug and corticosteroid, along with the permeation enhancer, if one is present in the formulation.

The reservoir matrix should be compatible with the drug, the corticosteroid and any carriers therefor. When using an aqueous based system, the reservoir matrix is preferably a hydrophilic polymer, e.g., a hydrogel. When using a non-aqueous based system, the reservoir matrix is preferably composed on a hydrophobic polymer. Suitable polymeric matrices are known in the transdermal drug delivery art and include, without limitation, natural and synthetic rubbers such as polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, silicones, butadiene/acrylonitrile copolymers, and ethylene vinyl acetate (EVA) polymers as described in U.S. Pat. No. 4,144,317, the disclosures of which are incorporated herein by reference. Other suitable materials include gelled or thickened mineral oil, petroleum jelly and various aqueous gels and cellulosic polymers. When a constant drug delivery rate is desired, the drug is present in the matrix or carrier at a concentration in excess of saturation, the amount of excess being a function of the desired length of the drug delivery period of the system. The drug may, however, be present at a level below saturation without departing from this invention as long as the drug and corticosteroid are continuously and co-extensively administered to the same skin or mucosa site at a rate and for a period of time sufficient to induce tolerance to the drug.

In addition to the sensitizing drug and the corticosteroid, which are essential to the invention, the reservoir matrix may also contain dyes, pigments, inert fillers, permeation enhancers (for either the drug, the corticosteroid or for both), excipients and other conventional components of pharmaceutical products or transdermal therapeutic systems known to the art.

As used herein the term "drug" relates to a biologically active agent, compound or composition of matter which can be transdermally and/or transmucosally administered to a human for the purpose of providing some beneficial or therapeutic effect. As used herein, the terms "transdermal administration" and "transmucosal administration" relate to the delivery of a drug by passage through intact human skin, mucosa and/or other body surfaces by topical application.

The present invention has utility in the transdermal and/or transmucosal administration of drugs which are sensitizing to humans when administered in therapeutically effective amounts. Examples of drugs which are suitable for transdermal and/or transmucosal administration and which are known to be sensitizing to humans include benzoyl peroxide, chlorpheniramine, clonidine, tetracaine, naloxone, nicotine, naltrexone, nalbuphine, propranolol, salbutamol, scopolamine, narcotic analgesics such as buprenorphine, hydromorphone and levorphanol. It is also anticipated that this invention has utility in connection with the delivery of other drugs which are within the broad class normally delivered through human body surfaces (e.g., skin) and membranes, and which are sensitizing to humans when administered in therapeutically effective amounts. In general, this includes therapeutic agents in all of the major therapeutic areas including, but not limited to, anti-infectives, such as antibiotics and antiviral agents, analgesics and analgesic combinations, anorexics, antiarthritics, antiasthmatic agents, anticonvulsants, antidepressants, antidiabetic agents, antidiarrheals, antihistamines, anti-inflammatory agents, antimigraine preparations, anti motion sickness preparations, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, beta-agonists, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

This invention contemplates the use of any corticosteroid including, without limitation, beclomethasone, betamethasone benzoate, betamethasone dipropionate, betamethasone valerate, clobetasol propionate, clobetasol butyrate, desonide, dexamethasone, diflorasone, fluocinonide, hydrocortisone, hydrocortisone esters such as hydrocortisone acetate, prednisolone and triamcinolone, for example.

Especially good results have been achieved using hydrocortisone or hydrocortisone acetate as the corticosteroid, optionally in combination with a skin permeation enhancer, such as an oily surfactant. However, sufficient hydrocortisone fluxes may be obtained when using no permeation enhancer or when the drug is carried by a pharmaceutically acceptable carrier which also acts to enhance hydrocortisone flux (e.g., ethanol). Corticosteroids more potent than hydrocortisone and hydrocortisone acetate typically do not require a permeation enhancer. However, even in cases where a corticosteroid permeation enhancer is needed, the advantages of hydrocortisone and hydrocortisone acetate are that they do not damage the skin upon prolonged exposure and they are approved for over-the-counter use.

For any given transdermal/transmucosal delivery system, certain parameters are predetermined. One such parameter is the therapeutically effective drug delivery rate, $J_d$ ($\mu g/cm^2$-hr). The therapeutically effective drug delivery rate and the drug delivery period depend upon a number of "non-system" factors including the drug itself, the condition for which the drug is being administered, the weight of the patient, etc. Once the therapeutically effective drug delivery rate and the desired drug delivery period are determined, the drug delivery system can be formulated. Given a set amount of drug in the delivery system and a set delivery time period t (hrs), the amount of drug which will be delivered per unit area $x_d$ ($\mu g/cm^2$) can be determined. In such systems, a sufficient amount of drug must be present in the reservoir to maintain the necessary concentration gradient which acts as the driving force to maintain the delivery rate for the predetermined delivery period, t (hrs). Normally, an excess of drug over saturation is used when a constant drug delivery rate is desired. Typically, this excess is calculated by determining the amount of drug needed to achieve saturation in the drug reservoir of the transdermal drug delivery system and adding to this value, the amount of drug which is going to be delivered ($x_d$) and an excess to act as a "safety factor" to provide continuous delivery at the required rates. The delivered amount is shown by the equation $x_d/J_d = t$ or $x_d = (J_d)(t)$.

In this invention, the corticosteroid is continuously and co-extensively administered with the sensitizing drug and to the same skin or mucosa site as the drug (i) at a rate and (ii) for a period of time sufficient to induce immune tolerance to the drug in the human. For any given drug and corticosteroid combination, the rate of corticosteroid administration and the length of time during which the drug and corticosteroid are co-extensively administered can be experimentally determined following the procedures outlined in the Examples. However certain general principles apply to all sensitizing drug/corticosteroid administrations. First, the corticosteroid is continuously and co-extensively administered to the same skin or mucosa site as the drug, for a period of time extending at least until the individual becomes tolerized to the drug. Thus until drug tolerance is induced, as long as the sensitizing drug is being administered to the skin or mucosa, the corticosteroid is also being administered to the same skin or mucosa site. Second, the corticosteroid delivery rate, $J_c$ ($\mu g/cm^2$-hr) is at least sufficient to prevent induction of sensitization to the drug being co-extensively administered. The $J_c$ value is the net delivery rate, taking into account the use of any permeation enhancers which help to achieve that rate.

Since the time t has already been determined by the therapeutic requirements of the system, the basic equation is $x_d/J_d = t = x_c/J_c$, where $x_c$ is the amount of corticosteroid per unit area which will be delivered to the skin. Just as with the drug, the corticosteroid is usually present in excess of saturation, to provide a constant delivery rate of the corticosteroid. The corticosteroid is continuously and co-extensively administered with the drug to a selected skin or mucosa site as long as any drug is being administered to the selected skin or mucosa site. Therefore, for a system where $J_d$, $x_d$, t and $J_c$ are known, the amount of corticosteroid to be placed in the system can be determined by calculating the amount needed to saturate the system plus the amount which is to be delivered ($x_c = (J_c)(t)$), plus an excess amount as a "safety factor".

The minimum required corticosteroid administration rate depends upon a number of factors including the type and amount of sensitizing drug being administered, the period of time over which the drug and corticosteroid are co-extensively administered, as well as the potency of the corticosteroid. For less potent corticosteroids such as hydrocortisone and hydrocortisone acetate, a typical minimum transdermal or transmucosal flux has been found experimentally to be in the range of about 0.05 to about 5 $\mu g/cm^2$-hr. For more potent corticosteroids such as betamethasone diproprionate, clobetasol propionate, diflorasone diacetate, dexamethasone and fluocinonide, a typical minimum transdermal or transmucosal flux is in the range of about 0.001 to about 0.05 $\mu g/cm^2$-hr. Because the more potent corticosteroids are effective at lower fluxes, there is usually no need to use permeation enhancers. However, with less potent corticosteroids such as hydrocortisone and hydrocortisone esters, a permeation enhancer may be necessary to achieve the necessary flux rate. Suitable permeation enhancers for corticosteroids are known to the art and include, without limitation, oily surfactants such as sucrose monolaurate and glycerol monooleate, alcohols and keratinolytic agents.

The minimum length of the continuous co-extensive administration period will vary depending upon the particular drug and corticosteroid being administered and the administration regimen for the drug. For example, the necessary time period of co-extensive administration of drug and corticosteroid will depend upon whether or not the drug is continuously delivered over the entire drug administration period or whether the drug is continuously delivered over only a portion of the entire drug administration period (e.g., as in Example I where the periods during which drug and corticosteroid are continuously and co-extensively administered are interspersed with periods during which no drug or corticosteroid is administered). Again, the minimum length of the co-extensive co-administration period is best determined for any particular drug and treatment regimen by routine experimentation following the time periods outlined in the examples as a guide. For specific drugs, suitable co-extensive administration periods have been experimentally determined. For example, in Example I, tolerance to dex-chlorpheniramine is induced in humans by continuously and coextensively administering the drug with hydrocortisone for at least about seven weeks over an entire drug administration period of about nine months. As described in Examples II through V, tolerance to naloxone hydrochloride can be induced in humans by continuously and co-extensively administering the drug with hydrocortisone for a period of at least about four weeks. Tolerance to clonidine can be induced in humans by continuously and co-extensively administering the drug with hydrocortisone for a period of at least about 10 weeks. Tolerance to nicotine can be induced in humans by continuously and co-extensively administering the drug with hydrocortisone for at least about one week. For tetracaine hydrochloride, continuous and co-extensive administration of the drug and hydrocortisone for at least about six weeks is sufficient to induce tolerance in humans to the drug. In all of these cases however, greater or lesser continuous and co-extensive administration periods may be sufficient to induce tolerance in humans, especially if other corticosteroids or other drug concentrations are utilized.

For very weakly sensitizing drugs, it may be possible in certain individual patients to induce tolerance to the drug by the application of a single transdermal or transmucosal drug delivery system. Known transdermal drug delivery systems have a drug delivery life of at most about 7 days (The reason for this is that after 7 days the skin under the delivery system sloughs off). This means that the system can only deliver materials transdermally for up to about 7 days after placement on the skin. However, in certain individual patients, tolerance to a weakly sensitizing drug can be induced by continuously and co-extensively administering the drug with a corticosteroid for a period of less than one week, e.g., 4 to 6 days. Examples of weakly sensitizing drugs suitable for transdermal or transmucosal administration include scopolamine, benzoyl peroxide and neomycin. As shown in Example VI, tolerance to scopolamine can be induced by applying a single transdermal delivery system on the skin of a human patient. During the first 4 to 5 days after the system is applied, the system continuously and co-extensively administers scopolamine and corticosteroid. Following the fifth day, the system administers only scopolamine. This can be accomplished in accordance with known methods of formulating the drug-containing and corticosteroid-containing reservoir(s) in the drug delivery system. Using such a system, certain individual patients will become tolerized to scopolamine after the 4 to 5 days of co-extensive administration with corticosteroid. Thereafter, the system delivers only scopolamine. By that time however, the patient has become tolerized to the drug. Accordingly, the patient suffers no sensitization and adverse skin reactions during the last 2 to 3 days of wearing the system, during which only scopolamine is being administered. Of course, thereafter the patient may receive subsequent drug delivery systems containing only scopolamine without adverse reaction as long as the tolerance to the drug is maintained.

The advantages of the present invention are best understood in light of the following examples which are illustrative of, but do not limit, the invention.

EXAMPLE I

The induction of tolerance to the sensitizing drug dex-chlorpheniramine maleate (DCPM) through the coextensive coadministration of DCPM and hydrocortisone, was tested on two groups (36 subjects in the experimental group and 20 subjects in a control group) of adult females. The experimental group (group I) received gels containing both DCPM and hydrocortisone. The group I gels contained by weight percent: 8% DCPM, 2% hydrocortisone, 4% hydroxyethylcellulose and the remainder comprising either (i) a mixture of sucrose monolaurate permeation enhancer and water or (ii) water alone. The control group (group II) received gels containing DCPM but no corticosteroid. The group II gels contained by weight percent: 8% DCPM, 4% hydroxyethyl cellulose and 88% water.

Both the group I and group II gels administered the DCPM at a transdermal flux of about 10–15 $\mu g/cm^2$-hr or about 0.5 to 0.7 mg/day for the 2 $cm^2$ system. For the gels containing hydrocortisone, the transdermal flux of the corticosteroid was about 0.05–1.0 682 $g/cm^2$-hr (the broad range of transdermal hydrocortisone flux was caused by the sucrose monolaurate being present in some of the gels but not in others) or about 0.002 to 0.05 mg/day for the 2 $cm^2$ system.

The gels were placed in standard 2 $cm^2$ patch test devices and applied under occlusion to rotating sites on the back and arms of each subject for three weeks. Over the three week period, the gels were exchanged every 48 to 72 hours. Over the three week period, nine gels were applied to the skin of each subject. After removal of the ninth gel, each of the subjects had no gel applied for a period of two weeks. At the expiration of the two week "gel free" period, each of the subjects in both groups received a group II type gel (i.e., a gel which contained DCPM but no hydrocortisone). Forty-eight hours later, the group II type gel was removed and another, similar one, applied to the same area. After an additional 48 hours the second gel was removed.

Reactions were observed 48 and 96 hours after the last gel removal. The results were as follows: in group II, 3 of the 20 subjects (15%) experienced sensitization, while in group I which used the gel containing hydrocortisone, none of the 36 subjects (0%) experienced any sensitization to the DCPM.

Fifteen weeks following the observations of the skin reactions in groups I and II, only the experimental group (group I) was further tested. The individuals in group I again received gels containing both DCPM and hydrocortisone. The gels contained by weight percent: 8% DCPM, 2% hydrocortisone, 4% hydroxyethylcellulose and the remainder comprising either (i) a mixture of a permeation enhancer (sucrose monolaurate) and water, or (ii) water alone. The gels contained up to 25 mg DCPM which administered the DCPM at a transdermal flux of about 10–15 ug/cm$^2$-hr or about 0.5 to 0.7 mg/day for the 2 cm$^2$ system. The transdermal flux of the corticosteroid was about 0.05–1.0 ug/cm$^2$-hr or about 0.002 to 0.05 mg/day for the 2 cm$^2$ system.

The gels were again placed in standard 2 cm$^2$ patch test devices and applied under occlusion to rotating sites on the back and arms of each subject for four weeks. Over the four week period, the gels were exchanged every 48 to 72 hours. Over the four week period, 12 gels were applied to the skin of each subject. After removal of the twelfth gel, each of the subjects received a group II type gel (i.e., a gel which contained DCPM but not hydrocortisone). Forty-eight hours later, the group II type gel was removed and another, similar one, applied to the same area. After an additional 48 hours, the second gel was removed. Reactions were observed 48 and 96 hours after the last gel removal. None of the 36 subjects (0%) experienced any sensitization to the DCPM.

Beginning ten days later, the same 36 individuals in the experimental group received a series of the same group II type gels (i.e., gels which contained DCPM but no hydrocortisone) over a period of three weeks. During the three week period, the gels were exchanged every 48 to 72 hours. Over the three week period, nine group II type gels were applied to rotating sites on the skin of each subject. After removal of the ninth gel, each of the subjects had no gel applied for a period of two weeks. At the expiration of the 2 week "gel free" period, each of the subjects received a group II type gel (i.e., a gel which contained DCPM but not hydrocortisone). Forty-eight hours later the group II type gel was removed and another, similar one, applied to the same area. After an additional 48 hours, the second gel was removed. Reactions were observed 48 and 96 hours after the last gel was removed. Again, none of the 36 subjects (0%) experienced sensitization.

The absence of any sensitization during and after the exposure and challenge to the gels containing DCPM but containing no hydrocortisone is significant. One would expect that the absence of any hydrocortisone administration during this approximately six-week period would have resulted in about 15% of the individuals in the experimental group becoming sensitized to the DCPM (as happened in the initial control experiment). Instead, it was found that none of the individuals became sensitized after prolonged (i.e., 25 days) exposure to the DCPM alone. The explanation for this is that the individuals in the experimental group had developed a tolerance to the DCPM as a result of the prior co-extensive administrations of DCPM and hydrocortisone. Once tolerization is induced, the administration of the tolerizing drug does not induce sensitization with the attendant skin reactions. Thus, the individual can receive prolonged transdermal or transmucosal administrations of the drug (i.e., the particular sensitizing drug for which that individual has become tolerized) without adverse reaction.

EXAMPLE II

Subjects in a control group each receive 4 successive 48 hour applications to different skin sites of aqueous gels containing 4% naloxone hydrochloride (at pH 7). 14 days later, each of the subjects in the control group receives a single 48 hour challenge (i.e., application to the skin) of an aqueous gel containing 4% naloxone hydrochloride (at pH 7). About 80% of the subjects become sensitized to the drug during the challenge.

Subjects in an experimental group each receive 12 successive applications at rotating sites of an aqueous gel containing 4% naloxone hydrochloride (at pH 7) and 2% hydrocortisone. Each of the 12 gels is applied for a period of 48 or 72 hours for a total continuous and co-extensive administration period of 28 days. Fourteen days after the 12th gel is removed, each of the subjects is challenged with a single gel containing 4% naloxone hydrochloride (at pH 7) applied for 48 hours. About 20% of the subjects become sensitized following the challenge. Immediately after the challenge, the non-sensitized subjects each receive 4 successive 48 hour applications of an aqueous gel containing 4% naloxone hydrochloride (at pH 7) but containing no hydrocortisone. Following this 8-day exposure to the naloxone hydrochloride alone, the subjects receive no gels for a period of two weeks. Following the 2-week "gel free" period, each of the subjects receives a 48 hour challenge application of a similar gel containing naloxone hydrochloride but not hydrocortisone. None of these individuals are sensitized upon challenge indicating that these individuals are tolerized to naloxone hydrochloride.

EXAMPLE III

A control group of white females each receive a polyisobutylene/mineral oil containing system with 12% clonidine and 1% of a permeation enhancer for 10 weeks. Each of the systems is applied continuously for 7 days to one site, but the next system is always applied to a different skin site. Twenty four hours after removal of each system (after 7 days wearing) the site is observed for signs of sensitization (e.g., erythema, edema, pustules). Following week five of wearing the systems, the first signs of sensitization are noted, and at the end of ten weeks, about 20% of the women are sensitized.

White women in an experimental group are each treated similarly, except that 0.1% hydrocortisone is added to the clonidine delivery systems. None of the women are sensitized after 10 weeks. On week 11 through 20, the women receive treatment identical to that extended to the first group, i.e. clonidine systems containing no hydrocortisone. At the end of this second ten week period, none of the subjects shows any degree of sensitization, thereby showing that they are tolerized to clonidine.

EXAMPLE IV

Subjects in a control group each receive a series of daily transdermal nicotine delivery systems consisting of ethylene vinyl acetate (EVA 40) and mineral oil. Each system contains 80 mg of nicotine. The systems are worn continuously for eight weeks (56 days). Each of the systems are worn for 24 hours and then immediately replaced with a new system which is reapplied to the same skin site. The site of application is observed for 48 hours following removal of the last system. At the end of the eight week test period, 25% of the subjects are sensitized.

Subjects in an experimental group each receive the same systems containing 1% hydrocortisone in addition to the 80 mg of nicotine, for one week. After a 10 day waiting period, the group is subjected to the same treatment as was applied to the first group (i.e., eight weeks of the nicotine only systems). None of the subjects are sensitized, showing that co-extensive administration of hydrocortisone and nicotine for one week induces tolerance to nicotine.

EXAMPLE V

Subjects in a control group each receive daily applications to rotating skin sites of aqueous gels (at pH 8) containing 2% tetracaine hydrochloride, for a period of four weeks. The skin sites are observed for sensitization 24 hours after removal of the last gel. About 70% of the subjects show signs of sensitization.

Subjects in an experimental group each receive daily applications to rotating skin sites of aqueous gels (at pH 8) containing 2% tetracaine hydrochloride and 1% hydrocortisone for six weeks. At the end of four weeks, about 15% of the subjects are sensitized. None of the remaining non-sensitized subjects show signs of sensitization during weeks five through six. At the end of the six week period, the non-sensitized subjects are treated with tetracaine gels containing no hydrocortisone for six additional weeks. No additional subjects become sensitized, indicating tolerization to tetracaine in these subjects.

EXAMPLE VI

Subjects in a control group each receive a series of three weekly transdermal scopolamine delivery systems having an area of two cm². Each system includes an impermeable polyethylene backing layer, a drug matrix comprising 53% polyisobutylene and 47% mineral oil, a microporous polyethylene rate controlling membrane and a contact adhesive layer comprising 53% polyisobutylene and 47% mineral oil. The drug matrix in each system is loaded with 1.5 wt% scopolamine. Each system delivers scopolamine at a transdermal flux of 0.15 $\mu$g/hr-cm² or 0.30 $\mu$g/hr for the 2 cm² system The systems are worn continuously for 3 weeks. Each of the systems are worn for 7 days and then immediately replaced with a new system which is reapplied to the same skin site. The site of application is observed for 48 hours following removal of the last system. At the end of the three week test period, about 5% of the subjects are sensitized.

Subjects in an experimental group each receive a transdermal scopolamine delivery system having the same construction and drug loading as the systems applied to the control group. For the systems applied to the experimental group, the contact adhesive layer is loaded with 1.1 wt% hydrocortisone. Each system continuously and co-extensively administers scopolamine and hydrocortisone for a period of 4 days, after which only scopolamine is delivered on days 5 through 7. Each of the systems delivers (i) scopolamine at a transdermal flux of 0.15 $\mu$g/hr-cm² or 0.30 $\mu$g/hr for the 2 cm² system over 7 days, and (ii) hydrocortisone at a transdermal flux of 0.10 $\mu$g/hr-cm² or 0.20 $\mu$g/hr for the 2 cm² system over 4 days. Immediately following the seventh day, the subjects in the group each receive a series of two weekly transdermal scopolamine delivery systems of the type applied to the control group. After the three week test period, none of the subjects are sensitized, showing that co-extensive administration of hydrocortisone and scopolamine for 4 days induces tolerance to scopolamine.

Although this invention has been described in detail in connection with certain preferred embodiments thereof, it will be understood that variations and modifications can be effected without departing from the spirit and scope of the invention as defined in the appended claims.

What is claimed is:

1. A method of inducing immune tolerance to a drug in a human, which drug is susceptible to inducing mucosal sensitization in the human when the drug is transmucosally administered at a therapeutically effective rate, comprising:

(a) continuously and co-extensively administering to the mucosa of the human:
   (1) the drug, to a selected mucosa site, at a therapeutically effective rate and over a predetermined delivery period; and
   (2) a corticosteroid, the corticosteroid being administered to the same selected site (i) at a rate and (ii) for a period of time sufficient to induce immune tolerance to the drug in the human; and thereafter (b) discontinuing the transmucosal administration of the corticosteroid to the human, and (c) transmucosally readministering the drug, without administering any corticosteroid, to the human, the drug being readministered at a therapeutically effective rate and for a period of time sufficient to maintain the induced immune tolerance in the human.

2. The method of claim 1, wherein said corticosteroid is transmucosally administered at a rate within the range of about 0.001–5 $\mu g/cm^2\text{-}hr$.

3. The method of claim 1, wherein the drug and the corticosteroid are co-extensively administered transmucosally from a matrix placed in drug and corticosteroid transmitting relationship to the mucosa.

4. The method of claim 1, wherein the sensitizing drug is selected from the group consisting of benzoyl peroxide, clonidine, scopolamine, tetracaine, chlorpheniramine, nicotine, naloxone, naltrexone, nalbuphine, propranolol, salbutamol, levorphanol, hydromorphone and buprenorphine.

5. The method of claim 1, wherein the corticosteroid is selected from the group consisting of hydrocortisone, hydrocortisone acetate, hydrocortisone esters, beclomethasone, betamethasone, betamethasone benzoate, betamethasone dipropionate, betamethasone valerate, clobetasol propionate, clobetasol butyrate, desonide, dexamethasone, diflorasone, fluocinonide and triamcinolone.

6. The method of claim 1, wherein the drug is administered to the human at a constant drug delivery rate over the predetermined delivery period.

7. The method of claim 1, wherein the corticosteroid is selected from the group consisting of hydrocortisone, hydrocortisone acetate and hydrocortisone esters.

8. The method of claim 7, including transmucosally administering a permeation enhancer with the corticosteroid, the permeation enhancer being effective to enhance the rate at which the corticosteroid is transdermally or transmucosally administered.

9. The method of claim 8, wherein the permeation enhancer is selected from the group consisting of oily surfactants, alcohols and keratinolytic agents.

10. The method of claim 9, wherein the permeation enhancer comprises an oily surfactant selected from the group consisting of sucrose monolaurate and glycerol monooleate.

11. The method of claim 1, wherein the drug and the corticosteroid are administered from an aqueous based formulation.

12. The method of claim 11, wherein the aqueous based formulation contains a gelling agent selected from the group consisting of hydroxyethylcellulose and hydroxypropylcellulose.

13. The method of claim 1, wherein the drug and the corticosteroid are administered from a non-aqueous based formulation containing a liquid selected from the group consisting of silicone fluid and mineral oil.

14. The method of claim 13, wherein the non-aqueous based formulation contains a gelling agent comprised of colloidal silicon dioxide.

15. The method of claim 1, wherein the drug comprises dex-chlorpheniramine maleate, the corticosteroid comprises hydrocortisone and the period of time is at least about seven weeks.

16. The method of claim 1, wherein the drug comprises naloxone hydrochloride, the corticosteroid comprises hydrocortisone and the period of time is at least about four weeks.

17. The method of claim 1, wherein the drug comprises clonidine, the corticosteroid comprises hydrocortisone and the period of time is at least about 10 weeks.

18. The method of claim 1, wherein the drug comprises nicotine, the corticosteroid comprises hydrocortisone and the period of time is at least about one week.

19. The method of claim 1, wherein the drug comprises tetracaine hydrochloride, the corticosteroid comprises hydrocortisone and the period of time is at least about six weeks.

20. The method of claim 1, wherein the drug comprises scopolamine, the corticosteroid comprises hydrocortisone and the period of time is about 4 to 6 days.

21. A transmucosal drug delivery system for transmucosally administering a drug to a human, which drug is weakly susceptible to inducing mucosal sensitization in the human when the drug is transmucosally administered at a therapeutically effective rate, comprising:
   (a) a matrix adapted to be placed in drug and corticosteroid transmitting relation to a selected site on the mucosa of the human, the matrix containing sufficient amounts of the drug and a corticosteroid to continuously and co-extensively administer to the same selected mucosa site:
   (1) the drug, at a therapeutically effective rate and over a delivery period of up to about 7 days; and
   (2) the corticosteroid, the corticosteroid being administered (i) at a rate and (ii) for a period of time sufficient to induce immune tolerance to the drug in the human;
   wherein the period of time sufficient to induce immune tolerance is no more than about 6 days, whereby after immune tolerance is induced, the matrix stops administering the corticosteroid and thereafter the matrix administers the drug to the human at a therapeutically effective rate and for a period of time sufficient to maintain the induced immune tolerance in the human.

22. The system of claim 21, wherein the matrix contains an amount of corticosteroid sufficient to transmucosally administer at a rate within the range of about 0.001-5 $\mu g/cm^2$-hr until immune tolerance is induced.

23. The system of claim 21, wherein the weakly sensitizing drug is selected from the group consisting of scopolamine, benzoyl peroxide and neomycin.

24. The system of claim 21, wherein the corticosteroid is selected from the group consisting of hydrocortisone, hydrocortisone acetate, hydrocortisone esters, beclomethasone, betamethasone, betamethasone benzoate, betamethasone dipropionate, betamethasone valerate, clobetasol propionate, clobetasol butyrate, desonide, dexamethasone, diflorasone, fluocinonide and triamcinolone.

25. The system of claim 21, wherein the drug is administered to the human at a constant drug delivery rate over a predetermined delivery period of about 5 to 7 days.

26. The system of claim 21, wherein the corticosteroid is selected from the group consisting of hydrocortisone, hydrocortisone acetate and hydrocortisone esters.

27. The system of claim 21, wherein the system contains and delivers a permeation enhancer which is effective to enhance the rate at which the corticosteroid is transmucosally administered.

28. The system of claim 27, wherein the permeation enhancer is selected from the group consisting of oily surfactants, alcohols and keratinolytic agents.

29. The system of claim 28, wherein the permeation enhancer comprises an oily surfactant selected from the group 30. The system of claim 21, wherein the matrix contains the drug and the corticosteroid in an aqueous based formulation.

31. The system of claim 30, wherein the aqueous based formulation contains a gelling agent selected from the group consisting of hydroxyethylcellulose and hydroxypropylcellulose.

32. The system of claim 21, wherein the matrix contains the drug and the corticosteroid in a non-aqueous based formulation containing a liquid selected from the group consisting of silicone fluid and mineral oil.

33. The system of claim 32, wherein the non-aqueous based formulation contains a gelling agent comprised of colloidal silicon dioxide.

34. The system of claim 21, wherein the drug comprises scopolamine, the corticosteroid comprises hydrocortisone and the period of time is about 4 to 5 days.

35. The system of claim 21, wherein the system includes an impermeable backing layer adjacent one surface of the matrix and a rate controlling membrane positioned between the matrix and the human mucosa.

36. The system of claim 21, wherein the system is adapted to be placed in drug and corticosteroid transmitting relation to the selected site using a pharmaceutically acceptable contact adhesive.

* * * * *